(12) United States Patent
Hayes et al.

(10) Patent No.: US 11,529,499 B2
(45) Date of Patent: Dec. 20, 2022

(54) APPARATUS AND METHODS FOR RESTORING TISSUE

(71) Applicant: Alucent Biomedical, Inc., Salt Lake City, UT (US)

(72) Inventors: Rb Eugene Hayes, Salt Lake City, UT (US); Steven A Tyler, Salt Lake City, UT (US)

(73) Assignee: Alucent Biomedical, Inc., Salt Lake City, UT (US)

( * ) Notice: Subject to any disclaimer, the term of this patent is extended or adjusted under 35 U.S.C. 154(b) by 197 days.

(21) Appl. No.: 16/686,879

(22) Filed: Nov. 18, 2019

(65) Prior Publication Data

US 2021/0146099 A1  May 20, 2021

(51) Int. Cl.
| | | |
|---|---|---|
| *A61M 25/10* | (2013.01) | |
| *A61N 5/06* | (2006.01) | |
| *A61M 25/00* | (2006.01) | |
| *A61B 18/18* | (2006.01) | |

(52) U.S. Cl.
CPC ............. *A61M 25/10* (2013.01); *A61B 18/18* (2013.01); *A61M 25/0026* (2013.01); *A61M 25/0045* (2013.01); *A61M 25/0082* (2013.01); *A61N 5/0601* (2013.01); *A61B 2018/1807* (2013.01); *A61M 2025/0004* (2013.01); *A61M 2025/0046* (2013.01); *A61M 2025/0062* (2013.01); *A61M 2025/1043* (2013.01); *A61M 2205/02* (2013.01); *A61M 2205/051* (2013.01)

(58) Field of Classification Search
CPC .......... A61B 18/24; A61B 2018/00107; A61B 2018/00285; A61B 2018/1807; A61M 2025/0004; A61M 2205/02; A61M 2205/051; A61M 25/10; A61M 2025/105; A61N 2005/0602; A61N 2005/063; A61N 5/0601; A61N 5/062
See application file for complete search history.

(56) References Cited

U.S. PATENT DOCUMENTS

| | | | |
|---|---|---|---|
| 6,468,244 B1 * | 10/2002 | Leone | A61L 29/103 424/9.36 |
| 2007/0282301 A1 * | 12/2007 | Segalescu | A61N 5/062 604/509 |

FOREIGN PATENT DOCUMENTS

WO  WO-2014022867 A1 *  2/2014  ............. A61F 2/945

* cited by examiner

*Primary Examiner* — Deanna K Hall
(74) *Attorney, Agent, or Firm* — Finnegan, Henderson, Farabow, Garrett & Dunner, LLP

(57) ABSTRACT

An apparatus and methods for tissue restoration are provided. The apparatus may include a catheter shaft extending from a proximal end to a distal tip, the catheter shaft defining lumens including an inflation lumen and a light fiber lumen, a coated balloon positioned on a translucent distal segment of the catheter shaft proximal to the distal tip in fluid communication with the inflation lumen, the coated distal balloon comprising a translucent material and a coated material on an outer surface of the coated balloon, and a light fiber positioned in the catheter shaft in the light fiber lumen and extending through the translucent distal segment.

19 Claims, 7 Drawing Sheets

APPARATUS AND METHODS FOR RESTORING TISSUE

BACKGROUND

Technical Field

The present disclosure generally relates to apparatus and methods to restore a vessel patency. More particularly, and without limitation, the disclosed embodiments relate to catheters, and catheter systems to create a natural vessel scaffolding and restore vessel patency.

BACKGROUND DESCRIPTION

Balloon catheters are used in a number of surgical applications including occluding blood flow either distally or proximally of a treatment site. The inflation of the balloon must be controlled in order to avoid over-expansion or breakage of the balloon, which may rupture or otherwise damage the vessel. Percutaneous Transluminal Angioplasty (PTA), in which a balloon is used to open obstructed arteries, has been widely used to treat atherosclerotic lesions. However, this technique is limited by the vexing problems of re-occlusion and restenosis. Restenosis results from the excessive proliferation of smooth muscle cell (SMC), and the rate of restenosis is above 20%. Thus, about one in five patients treated with PTA must be treated again within several months.

Additionally, stenting is a popular treatment, in which a constricted arteriosclerotic segment of the artery is mechanically expanded with the aid of a balloon catheter, followed by placement of a metallic stent within the vascular lumen to restore the flow of blood. Constriction or occlusion of the artery is problematic and can be itself, or cause, a major health complication(s). Intraluminal placement of a metallic stent has been found to result in the need for postoperative treatment in 20% to 30% of patients. One cause of this high frequency of required postoperative treatment is vascular intimal hyperplasia within the vascular lumen resulting in lumen narrowing despite the stent being placed. In order to decrease in-stent restenosis, attempts have been made to design a stent of a type having a surface carrying a restenosis-inhibiting drug so that when the stent is placed in an artery, the drug is eluted in a controlled manner within the vascular lumen. Those attempts have led to commercialization of drug-eluting stents (hereinafter referred to as DES) utilizing various drugs such as sirolimus (immunosuppressor) and paclitaxel (cytotoxic antineoplastic drug). However, since those drugs have an effect of inhibiting the proliferation of vascular cells (endothelial cells and smooth muscle cells) by acting on the cell cycle thereof, not only can the vascular intimal hyperplasia resulting from an excessive proliferation of the smooth muscle cells be suppressed, but proliferation is also suppressed of endothelial cells once denuded during placement of the stent. This can result in the adverse effect where the repair or treatment of the intima of a blood vessel becomes reduced. In view of the fact that thrombosis tends to occur more easily at a site less covered with endothelial cells in the intima of a blood vessel, an antithrombotic drug must be administrated for a prolonged time, say, half a year or so and, notwithstanding this antithrombotic drug administration, a risk of late thrombosis and restenosis will occur upon its discontinuance.

The technical problem addressed by the present disclosure is therefore to overcome these prior art difficulties by creating devices providing for controlled delivery of therapeutic agents to the surrounding tissues, propping a vessel open to a final shape, and functionalizing the therapeutic agent within the tissue and forming a cast shape, permitting blood flow and restoring tissue function. The solution to this technical problem is provided by the embodiments described herein and characterized in the claims.

SUMMARY

The embodiments of the present disclosure include catheters, catheter systems, and methods of forming a tissue scaffolding using catheter systems. Advantageously, the exemplary embodiments allow for controlled, uniform delivery of therapeutic agents to the surrounding tissues, casting the tissue to a final shape, and functionalizing the therapeutic agent in the tissue, forming the cast shape and propping the vessel open. The tissue may be a vessel wall of a vessel within the cardiovascular system.

According to embodiments of the present disclosure, an apparatus is provided. The apparatus may include a catheter shaft extending from a proximal end to a distal tip and having a translucent distal segment, the catheter shaft defining lumens including an inflation lumen and a light fiber lumen. The apparatus may further include a coated balloon positioned on the distal segment proximal to the distal tip in fluid communication with the inflation lumen, the coated distal balloon comprising a translucent material and a coated material on an outer surface of the coated balloon. The apparatus may also include a light fiber positioned in the catheter shaft in the light fiber lumen and extending through the distal segment.

In some embodiments, the inflation lumen provides an inflation fluid to the coated balloon, and a pressure of the inflation fluid in the coated balloon causes the coated balloon to expand into an expanded state.

In some embodiments, the coated material is a Natural Vascular Scaffolding treatment compound. The Natural Vascular Scaffolding compound may be light activated.

In some embodiments, the translucent material of the distal segment and the coated balloon is transparent. The light fiber may provide light activation through the distal segment and the coated balloon. The coated balloon may include material that conforms to the morphology of the vessel wall. The catheter shaft may be shielded along the length of the catheter shaft until the distal segment, allowing light transmission out of the distal segment and the coated balloon.

In some embodiments, the coated balloon has a compressed position that protects the coated material when the catheter shaft is guided to a target area of the vessel. The coated balloon may contact a vessel wall in a target area and the coated material transfers from the outer surface of the coated balloon to the target area. The catheter shaft may further define a guidewire lumen concentric with the catheter shaft. The light fiber lumen may extend to an opening in the distal tip, and the light fiber lumen is configured to receive a cooling agent that passes through the light fiber lumen and exits the light fiber through the opening in the distal tip.

According to another embodiment of the present disclosure, a method of tissue restoration in a blood vessel of a subject is provided. The method may include providing a catheter into the blood vessel. The catheter may include a catheter shaft extending from a proximal end to a distal tip and having a translucent distal segment, the catheter shaft defining lumens including an inflation lumen and a light fiber lumen. The apparatus may further include a coated balloon positioned on the distal segment proximal to the distal tip in fluid communication with the inflation lumen, the coated distal balloon comprising a translucent material and a coated material on an outer surface of the coated balloon. The apparatus may also include a light fiber positioned in the catheter shaft in the light fiber lumen and extending through the distal segment. The method may further include inflating the coated balloon to a predetermined pressure for a first predetermined amount of time, and activating a light source connected to the light fiber for a second predetermined amount of time after the first predetermined amount of time has completed, while keeping the coated balloon inflated, thereby providing light transmission through the distal segment and the coated balloon to activate the drug in the treatment area.

In some embodiments, the coated balloon is coated with a Natural Vascular Scaffolding treatment compound, the Natural Vascular Scaffolding compound is light activated. The light fiber may provide light activation through the distal segment and the coated balloon. The catheter shaft may be shielded along the length of the catheter shaft until the distal segment, thereby providing light transmission out of the distal segment and the coated balloon.

According to another embodiment of the present disclosure, an apparatus is provided. The apparatus may include a catheter shaft extending from a proximal end to a distal tip and having a translucent distal segment, the catheter shaft defining lumens including an inflation lumen and a light fiber lumen, a coated balloon positioned on the distal segment proximal to the distal tip in fluid communication with the inflation lumen, the coated distal balloon comprising a translucent material and a coated material on an outer surface of the coated balloon, and a light fiber positioned in the catheter shaft in the light fiber lumen and extending through the translucent distal segment. The catheter shaft may be shielded along the length of the catheter shaft until the distal segment, providing light transmission out of the distal segment and the coated balloon and the coated material is a light-activated treatment compound.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

The accompanying drawings constitute apart of this specification. The drawings illustrate several embodiments of the present disclosure and, together with the description, serve to explain the principles of the disclosed embodiments as set forth in the accompanying claims.

DETAILED DESCRIPTION

Reference will now be made in detail to embodiments and aspects of the present disclosure, examples of which are illustrated in the accompanying drawings. Where possible, the same reference numbers will be used throughout the drawings to refer to the same or like parts.

Figure 1:
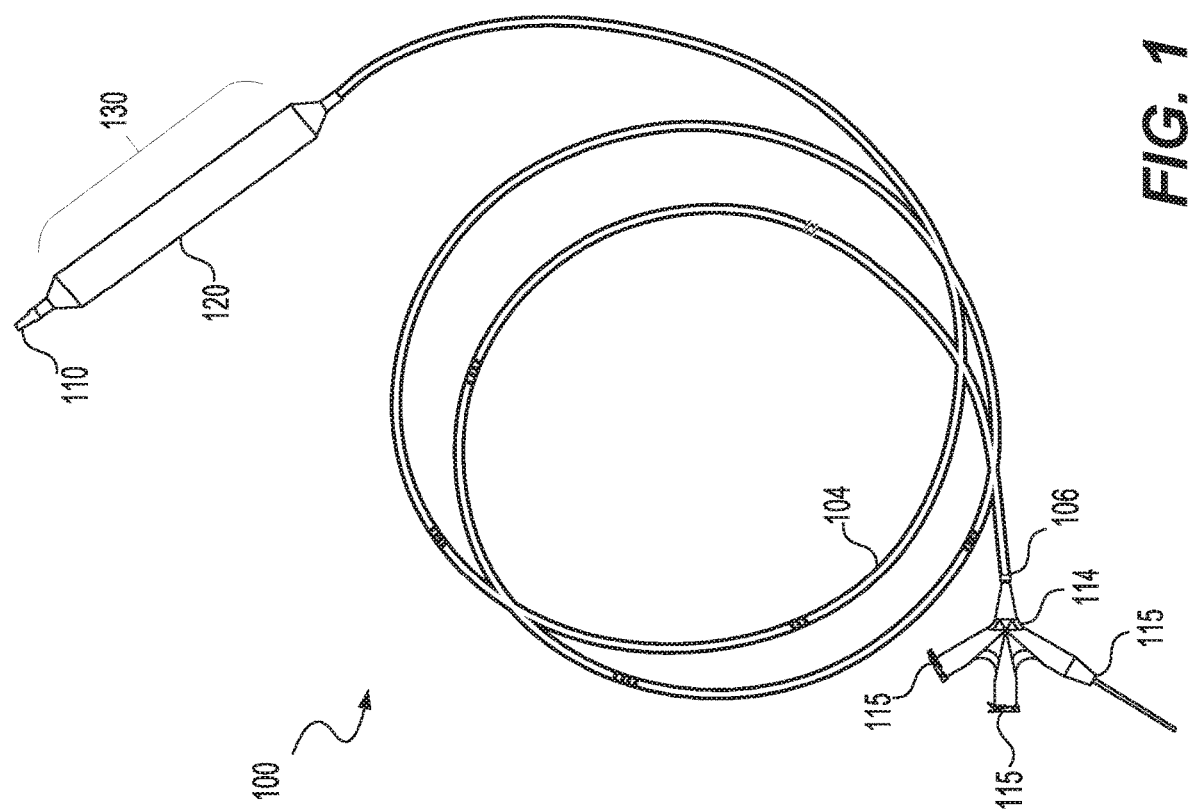
FIG. 1 is a side elevational view of an exemplary apparatus including a catheter, according to embodiments of the present disclosure.

FIG. 1 illustrates an apparatus 100 in accordance with an embodiment of this disclosure. The apparatus 100 having a catheter shaft 104 that extends from a proximal end 106 to a distal tip 110 of the apparatus 100. The apparatus 100 may be configured for longitudinal movement and positioning within a vessel (e.g. blood vessel) of a subject. In some embodiments, the apparatus 100 may be configured for treatment of an area of the vessel. In some embodiments, the apparatus 100 may occlude the vessel, while in other embodiments the apparatus may not occlude the vessel. For example, the apparatus 100 may be configured for delivery of a drug to an area of the vessel occupied by the apparatus 100 which may form and cast a shape in the vessel, as will be described in more detail below.

Figure 3:
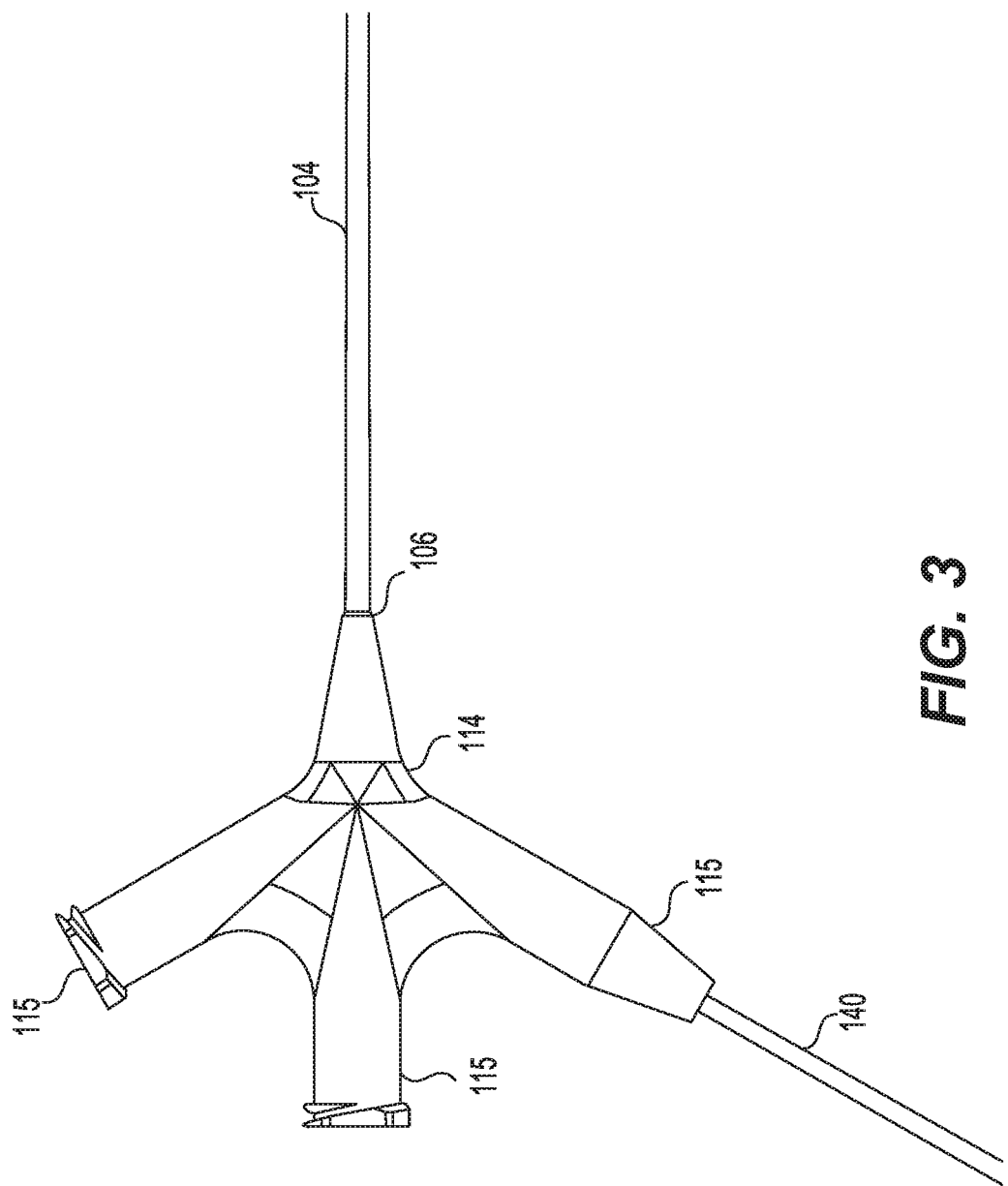
FIG. 3 is a side elevational view of a proximal portion of the catheter of FIG. 1.

The apparatus 100 may include a proximal end connector 114, shown in more detail at FIG. 3, positioned at the proximal end of the apparatus 100, and the catheter shaft 104 may extend in a distal direction therefrom. The catheter shaft 104 may define a plurality of lumens that are accessible via a plurality of ports 115 of the proximal end connector 114. The plurality of ports 115 may be configured to engage with external sources desirable to communicate with the plurality of lumens. The ports may engage with external sources via a variety of connection mechanisms, including, but not limited to, syringes, over-molding, quick-disconnect connectors, latched connections, barbed connections, keyed connections, threaded connections, or any other suitable mechanism for connecting one of the plurality of ports to an external source. Non-limiting examples of external sources may include inflation sources (e.g. saline solutions), gaseous sources, treatment sources (e.g. medication, drugs, or any desirable treatment agents discussed further below), light sources, among others. In some embodiments, apparatus 100 can be used with a guide wire (not shown), via guide wire lumen 164 (see FIG. 4), to assist in guiding the catheter shaft 104 to the target area of the vessel.

FIGS. 1-4 illustrate the apparatus 100 may include a coated balloon 120 positioned over a distal segment 130 of the catheter shaft 104 proximal to the distal tip 110. In some embodiments, the coated balloon 120 may be proximally offset from the distal tip 110 a distance between 0 mm and 1 mm, 0 mm and 2 mm, 0 mm and 3 mm, 0 mm and 10 mm, or 0 and 50 mm. The coated balloon 120 may take any shape suitable for supporting a wall of a blood vessel or other hollow body structure of the subject when the compliant or semi-compliant balloon is inflated. For example, the coated balloon 120 may expand into a cylindrical shape surrounding the distal segment 130 of the catheter shaft 104. The cylindrical shape may be gradually tapered inward at a proximal end and a distal end of the coated balloon 120, thereby providing a gradually tapered proximal end and distal end of the coated balloon 120 that taper into contact with and become flush with the catheter shaft 104.

Non-limiting examples of shapes the inflated coated balloon 120 may form include a cylindrical shape, football-shaped, spherical, ellipsoidal, or may be selectively deformable in symmetric or asymmetric shapes so as to limit the potential difference in the treated vessel shape and the untreated vessel shape reducing edge effects common between two surfaces of different stiffness as found in metal stents. The force exerted against a vessel interior by coated balloon 120 may be strong enough to scaffold the vessel wall with the apparatus 100 held in a stationary position within the vessel or other hollow body structure. However, the force is not so great as to damage the interior surface of the vessel or other hollow body structure. The coated balloon 120 may be substantially translucent.

The apparatus 100 may include a plurality of connectors 115 positioned proximally to the proximal end connector 114. For example, the coated balloon 120 may be terminated at the proximal end 106 with a connector capable of receiving an inflation source. In some embodiments, the connector may be a luer configuration. A center lumen (discussed in more detail below), may be terminated at the proximal end with a connector capable of receiving a fluid source for clearing the lumen from the proximal termination to outside the distal tip, and in some embodiments may include a luer configuration. The center lumen may also accommodate a guidewire for tracking the catheter apparatus to the desired anatomical location. As discussed in more detail below, the apparatus 100 may also include light fibers that may be terminated at the proximal end with an adaptor capable of connecting with a light source. Each light fiber may terminate with a separate and distinct adaptor or each light fiber may share an adaptor to a light source. The light fibers may be integrated into the apparatus 100.

The materials of the apparatus 100 may be biocompatible. The catheter shaft 104 may include material that is extrudable and capable of sustaining lumen integrity. The distal segment 130 of the catheter shaft 104 is substantially translucent to allow light transmission from light fibers. The catheter shaft 104 material is rigid enough to track over a guidewire and soft enough to be atraumatic. The catheter shaft 104 may be made of materials including, but not limited to polymers, natural or synthetic rubber, metal and plastic or combinations thereof, nylon, polyether block amide (PEBA), nylon/PEBA blend, thermoplastic copolyester (TPC), a non-limiting example may be HYTREL® (available from Dupont de Nemours, Inc. of Wilmington, Deleware), and polyethylene. The shaft materials can be selected so as to maximize column strength to the longitudinal length of the shaft. Further, the shaft materials can be braided, so as to provide sufficient column strength. The shaft materials can also be selected so as to allow the device to move smoothly along a guide wire. The catheter shaft 104 can also be provided with a lubricious coating as well as antimicrobial and antithrombogenic coatings. The shaft materials should be selected so as not to interfere with the efficacy of the agent to be delivered or collected. This interference may take the form of absorbing the agent, adhering to the agent or altering the agent in any way. The catheter shaft 104 of the present disclosure may be between about 2-16 French units ("Fr." where one French equals ⅓ of a millimeter, or about 0.013 inches). The catheter shafts to be used in coronary arteries may be between about 3-5 Fr. in diameter, and more specifically may be 3 Fr. The catheter shafts to be used in peripheral vessels may be between about 5-8 Fr. in diameter, and more specifically 5 Fr. The catheter shafts to be used in the aorta may be between about 8-16 Fr. in diameter, and more specifically 12 Fr.

The coated balloon 120 may be substantially translucent permitting light from light fibers to be transmitted substantially beyond the inflated diameter of the coated balloon 120. The coated balloon 120 may be compliant such that the material conforms substantially to a vessel's morphology. The coated balloon 120 material may be elastic, capable of elastically conforming substantially to a vessel's morphology thereby providing optimal drug delivery in a non-dilating and non-traumatic manner. The apparatus 100 may not cause any further trauma (e.g. trauma caused by atherectomy or percutaneous transluminal angioplasty "PTA" or vessel preparation methods) to the vessel to promote optimal healing.

Figure 2A:
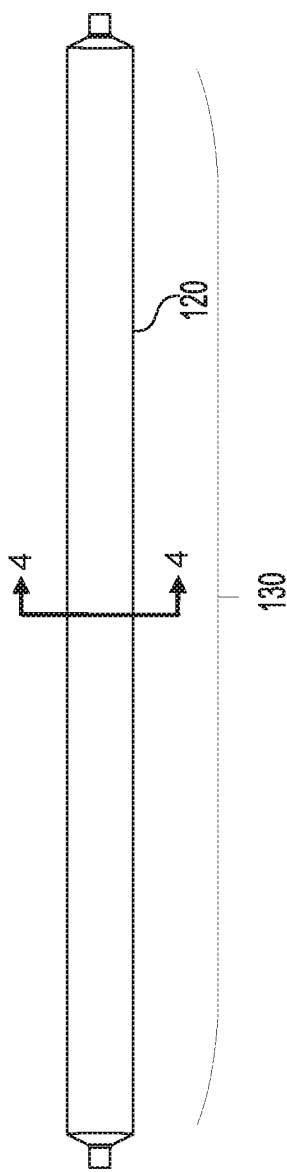
FIG. 2A is a side elevational view of a distal portion of the catheter of FIG. 1.
Figure 2B:
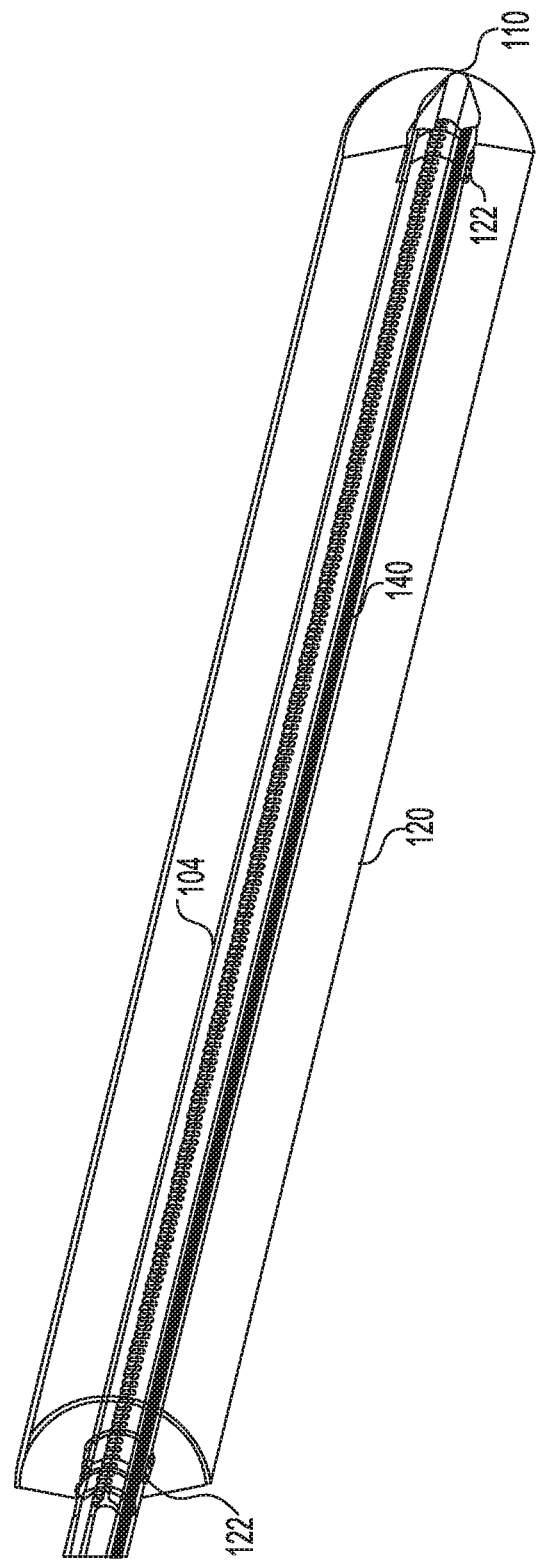
FIG. 2B is a perspective partial section view of the exemplary catheter of FIG. 2A.

FIGS. 2A and 2B illustrate the coated balloon 120 that may be coated with one or more drugs, e.g. with Natural Vascular Scaffolding (NVS) compound, which may be activated by light as discussed further below. The expansion of the coated balloon 120 may shape the treatment area (e.g. vessel) as desired and may provide the one or more drugs (e.g. NVS) coated on the external surface of the coated balloon 120 to the treatment area, as described in more detail below.

Figure 4:
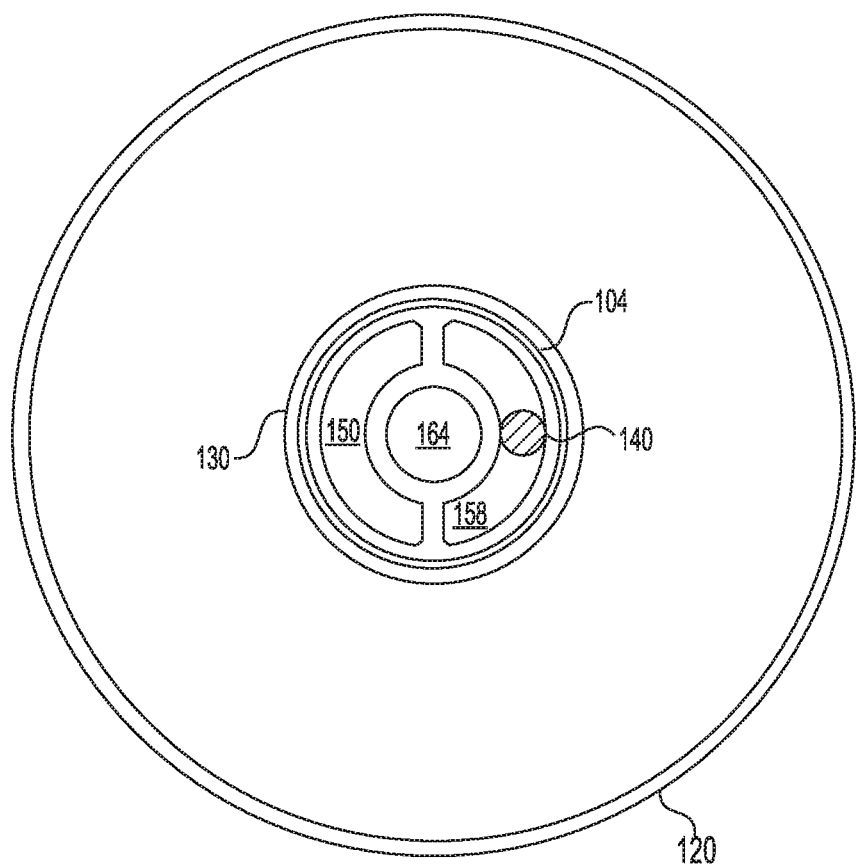
FIG. 4 is a cross-sectional view taken along line 4-4 of FIG. 2A.
Figure 5:
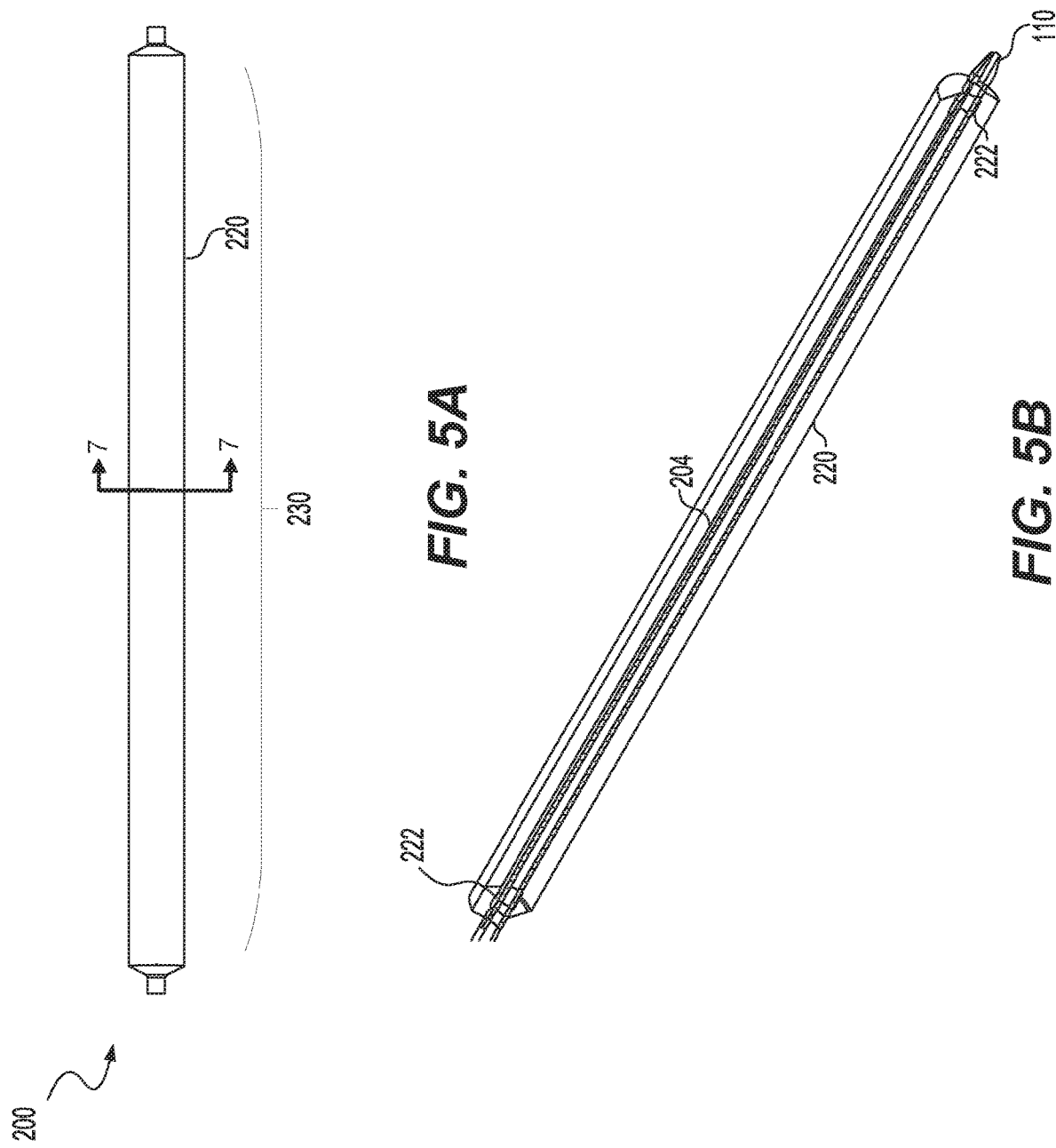
FIG. 5A is a side elevational view of a distal portion of another exemplary catheter according to embodiments of the present disclosure.
FIG. 5B is a perspective partial section view of the exemplary catheter of FIG. 5A.

The coated balloon 120 may be expandable from a folded or compressed position or orientation to an expanded position or orientation (FIG. 4). In some embodiments, the coated balloon 120 may be in a compressed position, which may be a folded configuration, when the catheter shaft 104 is guided to the target area of the vessel. The compressed or folded configuration may protect the coated material on the outside surface of the coated balloon 120 when the catheter shaft 104 is guided to a target area of the vessel. When the coated balloon 120 is positioned in the target area, the coated balloon 120 may be inflated into an expanded position.

The coated balloon 120 may include marker bands 122 positioned at a proximal end and a distal end of the coated balloon 120. The marker bands 122 may allow for precise location tracking of the coated balloon 120 during a procedure such that a user (e.g. a surgeon) may be able to readily locate the coated balloon 120 within an imaging system such as angiography. In some embodiments, the marker bands 120 may be radiopaque gold or platinum bands that are integrated into the apparatus 100.

In some embodiments, the light fiber 140 may be integrated into the apparatus 100. As used herein, the term "integrated" may refer to the light fiber being over molded into the apparatus 100 such that the light fiber becomes a non-interchangeable element of the apparatus 100. In other embodiments, as will be described below, the light fiber 140 may be removeable. In some embodiments, the light fiber may be integrated into the apparatus 100 at the time of manufacture. In other embodiments, the light fiber may be integrated into the apparatus 100 in a catheter lab during a clinical preparation process.

The light fiber 140 may be positioned in the catheter shaft 104 and extend through the distal segment 130. The light fiber 140 may transmit light through the distal segment 130 and the coated balloon 120. The light fiber 140 may be connected to the proximal end connector 114 and may have proximal ends that connect to a light fiber activation source via at least one of the plurality of ports 115. In some embodiments, the light fiber 140 may be configured to transmit light at a wavelength of 375 nanometers (nm) to 475 nm, and more specifically 450 nm that transmits through the distal segment 130 and the coated balloon 120. The light fiber 140 may emit light outside of the ultraviolet (UV) range of 10 nm to 400 nm. In some embodiments, the light fiber 140 may be positioned in the light fiber lumen 158, and the light fiber 140 may be covered or shielded along the length of the catheter shaft 104 so that light is only transmitted out of the distal segment 130 and the coated balloon 120.

In some embodiments, the light fiber 140 may be made from plastic core and cladding. The refractive index of the core is high. The refractive index of the cladding is low. A non-limiting example of the core material may be polymethyl methacrylate (PMMA). A non-limiting example of the cladding may be a silicone material. The light source may control the wavelength and supplied power of the light fibers 140. The pattern of the breaks in the cladding of the light fiber ensure uniform power distribution to the vessel wall. Longer lengths have a different pattern than shorter lengths. The distal lengths of cladding breaks are matched to the length of the balloons.

FIG. 4 is a cross-sectional view taken along line 4-4 of FIG. 2 showing a plurality of lumens within the assembly 100, according to an embodiment of this disclosure. The catheter shaft 104 may have an outside diameter and outside surface 130. The catheter shaft 104 may have an inside configuration of three distinct and separate lumens, extending from the proximal end 106 to the distal tip 110.

The coated balloon 120 may be in fluid communication with an inflation lumen 150. The inflation lumen 150 may extend through the catheter shaft 104 and have an input at one of the plurality of ports 115 of the proximal end connector 114. Fluid communication between the coated balloon 120 and the inflation source via the inflation lumen 150 may cause the coated balloon 120 to selectively fill and expand.

A light fiber lumen 158 may be provided. A light fiber lumen may be positioned in the catheter shaft 104 to receive one or more light fibers, and the light fiber lumen 158 may extend from the proximal end 106 into the distal segment 130. In another exemplary embodiment, the catheter shaft 104 may include a plurality of light fiber lumens.

In some embodiments, the light fiber lumen 158 may extend from the proximal end 106 to the distal tip 110 and may include an opening at each of the proximal end 106 and the distal tip 110. The light fiber lumen 158 may be configured to receive a cooling supply from the proximal end that may communicate a cooling agent (e.g. a fluid such as a saline solution), and the opening at the distal tip 110 may allow the cooling agent to pass through the light fiber lumen 158 and exit through the opening at the distal tip 110 of the light fiber lumen 158. In such embodiments, the cooling agent passing through the light fiber lumen 158 may surround the light fiber 140 and provide temperature regulation to the light fiber 140.

A guidewire lumen 164 may also be provided. A guidewire lumen may be concentric with the catheter shaft outside diameter and may be arranged in the catheter shaft 104, from the proximal end 106 through the distal tip 110. The guidewire lumen 164 may accommodate a guidewire to aid the placement of the apparatus 100 to a desired anatomical position communicating with the proximal end and distal tip. The guidewire may be separate and distinct from the apparatus 100 and extend proximally beyond the proximal end and distally beyond the distal tip of the catheter shaft. The guidewire lumen 164 is located concentric with the catheter outer diameter; the catheter shaft is oriented concentrically with the guidewire permitting the catheter shaft 104 to follow the guidewire without favoring one side of the catheter shaft 104 or whipping from side to side. The guidewire may remain in the guidewire lumen 104 maintaining anatomical position during the activation of the light fibers.

As shown, the catheter shaft 104 may a three-lumen extrusion of the inflation lumen 150, the light fiber lumen 158 and the guidewire lumen 164. The guidewire lumen 164 may be concentrically positioned within the catheter shaft 104 between the inflation lumen 150 and the light fiber lumen 158. The inflation lumen 150 and the light fiber lumen 158 may have a semi-circular or hemi-circular cross-sectional shape and may in combination surround the guidewire lumen 164 that is centrally positioned between the inflation lumen 150 and the light fiber lumen 158.

In some embodiments, the apparatus 100 may include a two-lumen extrusion instead of the three-lumen extrusion shown in FIG. 4. In such an embodiment, one lumen may be configured to receive a guidewire and the other lumen may be configured to receive a light fiber and be connected to an inflation source so that the inflation source can fluidically communicate with the coated balloon 120.

FIGS. 5A to 7 show another embodiment of an apparatus 200 having a coated balloon 220 with a catheter shaft 204 that receives a light fiber 240 that is removeable. The coated balloon 220 may have the same or similar features to coated balloon 120 described above. The apparatus 200 may share many of the same components and features of apparatus 100 described above.

The coated balloon 220 is positioned over a distal segment 230 of the catheter shaft 204 proximal to the distal tip 210. In some embodiments, the coated balloon 220 may be proximally offset from the distal tip 110 a distance between 0 mm and 1 mm, 0 mm and 2 mm, 0 mm and 3 mm, 0 mm and 10 mm, or 0 and 50 mm. The coated balloon 220 may take any shape suitable for supporting a wall of a blood vessel or other hollow body structure of the subject when the compliant or semi-compliant balloon is inflated, as described above in reference to the coated balloon 220.

The coated balloon 220 may include marker bands 222 positioned at a proximal end and a distal end of the coated balloon 220. The marker bands 222 may allow for precise location tracking of the coated balloon 220 during a procedure such that a user (e.g. a surgeon) may be able to readily locate the coated balloon 220 within an imaging system. In some embodiments, the marker bands 220 may be radiopaque gold or platinum bands that are integrated into the apparatus 200.

Figure 6:
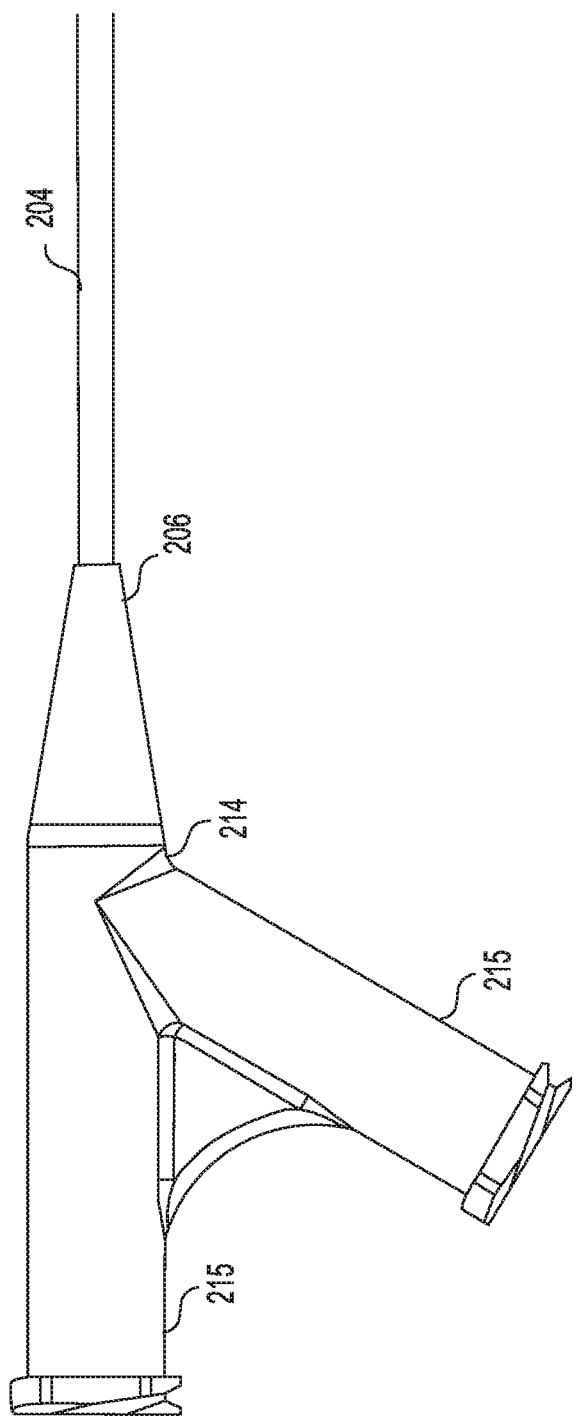
FIG. 6 is a side elevational view of a proximal portion of the catheter of FIG. 5A.

The apparatus 200 may include a proximal end connector 214, shown in more detail at FIG. 6, positioned at the proximal end of the apparatus 200, and the catheter shaft 204 may extend in a distal direction therefrom. The catheter shaft 204 may define lumens that are accessible via one or more of ports 215 of the proximal end connector 214. The ports 215 may be configured to engage with external sources desirable to communicate with the plurality of lumens. The ports may engage with external sources via a variety of connection mechanisms, including, but not limited to, syringes, over-molding, quick-disconnect connectors, latched connections, barbed connections, keyed connections, threaded connections, or any other suitable mechanism for connecting one of the plurality of ports to an external source. Non-limiting examples of external sources may include inflation sources (e.g. saline solutions), gaseous sources, treatment sources (e.g. medication, drugs, or any desirable treatment agents discussed further below), light sources, among others. In some embodiments, apparatus 200 can be used with a guide wire (not shown), via guide wire lumen 264 (see FIG. 7), to assist in guiding the catheter shaft 204 to the target area of the vessel.

Figure 7:
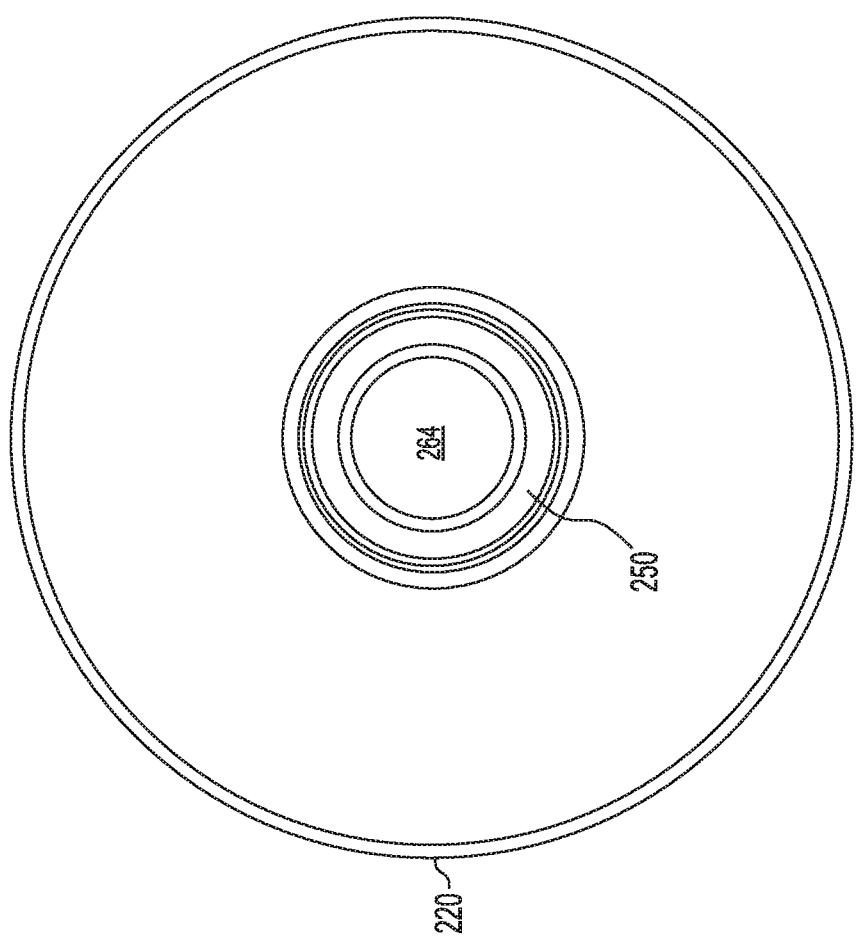
FIG. 7 is a cross-sectional view taken along line 7-7 of FIG. 5A.

FIG. 7 is a cross-sectional view taken along line 7 to 7 of FIG. 5A showing the lumens within the assembly 200, according to an embodiment of this disclosure. The catheter shaft 104 may have an inside configuration of two distinct and separate lumens, extending from the proximal end 206 to the distal tip 210.

The coated balloon 220 may be in fluid communication with an inflation lumen 250. The inflation lumen 250 may extend through the catheter shaft 204 and have an input at one of the ports 215 of the proximal end connector 214. Fluid communication between the coated balloon 220 and the inflation source via the inflation lumen 250 may cause the coated balloon 220 to selectively fill and expand.

A light fiber lumen 264 may be positioned in the catheter shaft 204 to receive light fibers and guide wires, and the light fiber lumen 264 may extend from the proximal end 206 into the distal segment 230. The light fiber lumen 264 may be concentric with the catheter shaft 204 and the inflation lumen 250 and may be arranged in the catheter shaft 204, from the proximal end 206 through the distal tip 210. The light fiber lumen 264 may accommodate a guidewire to aid the placement of the apparatus 200 to a desired anatomical position communicating with the proximal end and distal tip. The guidewire may be separate and distinct from the apparatus 200 and extend proximally beyond the proximal end and distally beyond the distal tip of the catheter shaft. The guidewire lumen 264 is located concentric with the catheter outer diameter, the catheter shaft is oriented concentrically with the guidewire permitting the catheter shaft 204 to follow the guidewire without favoring one side of the catheter shaft 204 or whipping from side to side. The guidewire may remain in the light fiber lumen 264 maintaining anatomical position during the activation of the light fibers.

The light fiber may be removeable and may be inserted through the light fiber lumen 264 to be positioned in the catheter shaft 204 and extend through the distal segment 230. The light fiber may transmit light through the distal segment 230 and the coated balloon 220. The light fiber may be connected to the proximal end connector 214 and may have proximal ends that connect to a light fiber activation source via at least one of the ports 215. In some embodiments, the light fiber may be configured to transmit light at a wavelength of 375 nanometers (nm) to 475 nm, and more specifically 450 nm that transmits through the distal segment 230 and the coated balloon 220. The light fiber may emit light outside of the ultraviolet (UV) range of 10 nm to 400 nm. In some embodiments, the light fiber may be positioned in the light fiber lumen 264, and the light fiber may be covered or shielded along the length of the catheter shaft 204 so that light is only transmitted out of the distal segment 230 and the coated balloon 220.

Now that the components of each apparatus 100, 200 have been described in detail, the methods associated with both apparatuses 100 and 200 can be appreciated. The target area for a delivery of drug source may be a vessel of the cardiovascular system. In some embodiments, the target area may be first prepared by percutaneous transluminal angioplasty (PTA) or atherectomy to displace or remove damaged vessel cellular debris. The catheter apparatus 100, 200 may not be intended to replace PTA; the functional pressure of the coated balloon 120, 220 is only sufficient to prop open the vessel during drug functionalization. The coated balloon 120, 220 may be inflated which into contact with the vessel wall in order to uniformly deliver the coated drug to the vessel wall. While in this vessel supported position, a light source may be supplied to the light fibers 140 in the catheter shaft 104, 204 for transmittance through the catheter shaft 104, 204, through the coated balloon 120, 220 and into the vessel wall.

An embodiment of this disclosure provides an exemplary method of tissue restoration in a blood vessel of a subject. The method may include providing an apparatus (e.g. apparatus 100, 200) and preparing the apparatus for a clinical procedure, which may include sterilizing the apparatus and connecting the light fiber to the light source. The method may further include advancing the apparatus to the treatment site over a guidewire using angiography for visualization and aligning the marker bands with the desired treatment site. Subsequently, the balloon may be inflated to a desired pressure based on a sizing chart for the treatment area (e.g. based on the diameter of the treatment vessel) and maintain the inflation of the balloon a predetermined amount of time (e.g. one to three minutes), allowing the drug to transfer into the wall of the artery.

The method may further include, while the balloon remains inflated, turning on the light source for a predetermined amount of time (e.g. one to three minutes), transmitting light down the light fiber and allowing the light to activate the drug that has been transported into the artery. Once complete, the balloon may be deflated and removed.

Another embodiment of this disclosure includes an exemplary method of tissue restoration in a blood vessel of a subject. The method may include providing an apparatus (e.g. apparatus 100, 200) and preparing the apparatus for a clinical procedure, which may include sterilizing the apparatus and connecting the light fiber to the light source. The method may further include advancing the apparatus to the treatment site over a guidewire using angiography for visualization and aligning the marker bands with the desired treatment site. Subsequently, the balloon may be inflated to a desired pressure based on a sizing chart for the treatment area (e.g. based on the diameter of the treatment vessel) and maintain the inflation of the balloon a predetermined amount of time (e.g. one to three minutes), allowing the drug to transfer into the wall of the artery.

The method may further include, while the balloon remains inflated, removing the guidewire and placing the light fiber down the guidewire lumen. Once the light fiber is in position, the method includes turning on the light source for a predetermined amount of time (e.g. one to three minutes), transmitting light down the light fiber and allowing the light to activate the drug that has been transported into the artery. Once complete, the light fiber may be removed, and the guidewire may be placed back into the apparatus so that the deflated balloon may be removed.

In some embodiments, the drug is not cured or activated, but the drug is functionalized to cross-link with tissue proteins. The tissue proteins, the drug, and the light may be present to create a therapeutic effect. The functionalizing of the drug may not be time dependent, but instantaneous or nearly so, dependent on wavelength alone at the proper intensity. The light power compensates for losses through the light fiber, balloon, and tissue wall and may be balanced to avoid heat buildup during therapy. Additionally or alternatively, the functionalizing of the drug may be correlated to the light power that is oscillated, pulsed, or is off-duty cycled where the light power is on for a period of time and off for another period of time. In some embodiments, the duty cycle may be 10%, which means the light power is on for 10% of the time and off for 90% of the time. In other embodiments, the duty cycle may be 20%, 30%, 40%, 50%, 60%, 70%, 80%, or 90%.

Additionally, therapeutic agents useful with the device of the present disclosure include any one of or a combination of several agents which are gas, liquid, suspensions, emulsions, or solids, which may be delivered or collected from the vessel for therapeutic or diagnostic purposes. Therapeutic agents may include biologically active substances, or substances capable of eliciting a biological response, including, but not limited to endogenous substances (growth factors or cytokines, including, but not limited to basic fibroblast growth factor, acidic fibroblast growth factor, vascular endothelial growth factor, angiogenic factors, microRNA), viral vectors, DNA capable of expressing proteins, sustained release polymers, and unmodified or modified cells. Therapeutic agents may include angiogenic agents which induce the formation of new blood vessels. Therapeutic agents may also include anti-stenosis or anti-restenosis agents which are used to treat the narrowing of blood vessel walls. Therapeutic agents may include light-activated agents such as light-activated anti-stenosis or light-activated anti-restenosis agents that may be used to treat the narrowing of blood vessel walls.

Accordingly, apparatus 100 is multifunctional, providing drug delivery control in open and closed positions, and propping open a vessel wall forming a shape during drug functionalizing with a light source of a specific wavelength outside of the ultraviolet (UV) range (10 nm to 400 nm).

Accordingly, the apparatus and methods described herein provide the delivery of NVS to a treatment area (e.g. a vessel) and provide restoration to that treatment area using the apparatus or according to the methods described above. The apparatus and method described above provide concurrently treating the vessel with one or more drugs (e.g. with Paclitaxel and NVS) with minimal loss to other vessels, scaffolding and casting the vessel, and light activation of the one or more drugs delivered to the treatment area. These advantages can be accomplished utilizing the apparatus and methods described herein.

According to embodiments of the present disclosure, the NVS compound may include dimeric naphthalmides as described in U.S. Pat. No. 6,410,505 B2, and U.S. Provisional Patent Application No. 62/785,477. For example, a dimeric naphthalimide compound, 2,2'-((ethane-1,2-diylbis (oxy))bis(ethane-2,1-diyl))bis(6-((2-(2-(2-aminoethoxy) ethoxy)ethyl)amino)-1H-benzo[de]isoquinoline-1,3(2H)-dione), also known as 10-8-10 dimer, 6-[2-[2-(2-aminoethoxy) ethoxy]ethylamino]-2-[2-[2-[2-[6-[2-[2-(2-aminoethoxy) ethoxy]ethylamino]-1,3-dioxobenzo[de]isoquinolin-2-yl] ethoxy]ethoxy]ethyl]benzo[de]isoquinoline-1,3-dione; 2,2'-[1,2-ethanediylbix(oxy-2,1-ethanediyl)]bis[6-({2-[2-(2-aminoethoxy)ethoxy]ethyl}amino)-1H-benzo[de] isoquinoline-1,3(2H)-dione]; and 1H-benz[de]isoquinoline-1,3(2H)-dione, 2,2'-[1,2-ethanediylbis(oxy-2,1-ethanediyl)] bis[6-[[2-[2-(2-aminoethoxy)ethoxy]ethyl]amino]-(9Cl), and herein referred to as Compound of Formula (I), has been disclosed. Id.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware and software, but systems and methods consistent with the present disclosure can be implemented as hardware alone. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure (e.g., slitted apertures, apertures, perforations may be used interchangeably maintaining the true scope of the embodiments)

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. An apparatus comprising
   a catheter shaft extending from a proximal end to a distal tip and having a translucent distal segment, the catheter shaft defining lumens including an inflation lumen and a light fiber lumen;
   a coated balloon positioned on the distal segment proximal to the distal tip in fluid communication with the inflation lumen, the coated distal balloon comprising a translucent material and a coated material on an outer surface of the coated balloon; and
   wherein, in use, the coated balloon is configured to at least partially contact the vessel wall in an expanded state; and
   wherein the coated balloon is configured so that a therapeutically effective quantity of the coated material is transferred from the outer surface of the coated balloon to the target area when the coated balloon contacts a vessel wall in a target area in an expanded state; and
   a light fiber positioned in the catheter shaft in the light fiber lumen and extending through the distal segment.

2. The apparatus of claim 1, wherein the inflation lumen provides an inflation fluid to the coated balloon, and a pressure of the inflation fluid in the coated balloon causes the coated balloon to expand into an expanded state.

3. The apparatus of claim 1, wherein the coated material is a Natural Vascular Scaffolding treatment compound.

4. The apparatus of claim 3, wherein the Natural Vascular Scaffolding compound is light activated.

5. The apparatus of claim 1 wherein the translucent material of the distal segment and the coated balloon is transparent.

6. The apparatus of claim 1 wherein the light fiber provides light activation through the distal segment and the coated balloon.

7. The apparatus of claim 1, wherein the coated material on the coated balloon conforms to the morphology of the vessel wall.

8. The apparatus of claim 1, wherein the catheter shaft is shielded along the length of the catheter shaft until the distal segment, allowing light transmission out of the distal segment and the coated balloon.

9. The apparatus of claim 1, wherein the coated balloon has a compressed position that protects the coated material when the catheter shaft is guided to a target area of the vessel.

10. The apparatus of claim 1, wherein the catheter shaft further defines a guidewire lumen concentric with the catheter shaft.

11. The apparatus of claim 1, wherein the light fiber lumen extends to an opening in the distal tip.

12. The apparatus of claim 11, wherein the light fiber lumen is configured to receive a cooling agent that passes through the light fiber lumen and exits the light fiber through the opening in the distal tip.

13. The method of claim 11, wherein the catheter shaft is shielded along the length of the catheter shaft until the distal segment, thereby providing light transmission out of the distal segment and the coated balloon.

14. A method of tissue restoration in a blood vessel of a subject comprising:
 providing a catheter into the blood vessel, the catheter comprising:
  a catheter shaft extending from a proximal end to a distal tip and having a translucent distal segment, the catheter shaft defining a plurality of lumens including an inflation lumen, a guidewire lumen, and a light fiber lumen;
  a drug coated balloon positioned on the distal segment proximal to the distal tip in fluid communication with the inflation lumen, the drug coated distal balloon comprising a translucent material; and
  a light fiber positioned in the catheter shaft in the light fiber lumen and extending through the distal segment;
 inflating the coated balloon to a predetermined pressure for a first predetermined amount of time to allow the coated drug to transfer to a target area;
 activating a light source connected to the light fiber for a second predetermined amount of time after the first predetermined amount of time has completed, while keeping the drug coated balloon inflated, thereby providing light transmission through the distal segment and the coated balloon to activate the drug in the target area to form a cast shape and to prop the vessel open.

15. The method of claim 14 wherein the coated balloon is coated with a Natural Vascular Scaffolding treatment compound.

16. The method of claim 15, wherein the Natural Vascular Scaffolding compound is light activated.

17. The method of claim 14 wherein the translucent material of the distal segment and the coated balloon is transparent.

18. The method of claim 14 wherein the light fiber provides light activation through the distal segment and the coated balloon.

19. An apparatus comprising
 a catheter shaft extending from a proximal end to a distal tip and having a translucent distal segment, the catheter shaft defining lumens including an inflation lumen and a light fiber lumen;
 a coated balloon positioned on the distal segment proximal to the distal tip in fluid communication with the inflation lumen, the coated distal balloon comprising a translucent material and a coated material on an outer surface of the coated balloon; and
 wherein, in use, the coated balloon is configured to at least partially contact a vessel wall in an expanded state; and
 wherein the coated balloon is configured so that a therapeutically effective quantity of coated material is transferred from the outer surface of the coated balloon to the target area when the coated balloon contacts the vessel wall in a target area in an expanded state;
 a light fiber positioned in the catheter shaft in the light fiber lumen and extending through the translucent distal segment;
 wherein the catheter shaft is shielded along the length of the catheter shaft until the distal segment, providing light transmission out of the distal segment and the coated balloon and the coated material is a light-activated treatment compound.

* * * * *